United States Patent [19]

Lemelson

[11] Patent Number: 5,738,102
[45] Date of Patent: Apr. 14, 1998

[54] PATIENT MONITORING SYSTEM

[76] Inventor: Jerome H. Lemelson, Suite 286, Unit 802 930 Tahoe Blvd., Incline Village, Nev. 89451-9436

[21] Appl. No.: 690,028

[22] Filed: Jul. 31, 1996

Related U.S. Application Data

[63] Continuation of Ser. No. 221,045, Mar. 31, 1994, abandoned.

[51] Int. Cl.[6] .................................................. A61B 5/0205
[52] U.S. Cl. .......................... 128/671; 128/903; 128/670; 128/696; 128/700; 128/715; 128/782; 128/701
[58] Field of Search ....................... 607/18–21, 4; 128/670, 671, 696, 700, 715, 903, 701, 782

[56] References Cited

U.S. PATENT DOCUMENTS

| | | | |
|---|---|---|---|
| 4,250,888 | 2/1981 | Grosskopf | 128/702 |
| 4,299,233 | 11/1981 | Lemelson | 128/687 |
| 4,886,064 | 12/1989 | Strandberg | 607/18 |
| 4,889,131 | 12/1989 | Salem et al. | 128/700 |
| 4,952,928 | 8/1990 | Carroll et al. | 128/903 |
| 4,974,607 | 12/1990 | Miwa | 128/903 |
| 5,014,698 | 5/1991 | Cohen | 607/4 |
| 5,036,869 | 8/1991 | Inahara | 128/696 |
| 5,042,497 | 8/1991 | Shapland | 607/4 |
| 5,269,301 | 12/1993 | Cohen | 607/18 |

*Primary Examiner*—William E. Kamm
*Assistant Examiner*—Kennedy J. Schaetzle
*Attorney, Agent, or Firm*—Niro, Scavone, Haller & Niro

[57] ABSTRACT

A system for monitoring and computer analyzing select physiological variables of a patient in real time in order to alert medical personnel to the need for medical treatment or automatically administering such treatment under computer control. Such physiological variables monitored by the system may include lung sounds, respiratory rate and rhythm, heart rate and rhythm, heart sounds, and body temperature. Coded signals relating to the physiological variables are produced and compared with reference versions of same by a decision computer in order to evaluate the patient's condition. If the evaluation indicates medical treatment is needed, the decision computer activates a local and/or a remote alarm to alert medical personnel and/or activates one or more actuators for adminstering a medical treatment such as the injection or infusion of a drug.

20 Claims, 1 Drawing Sheet

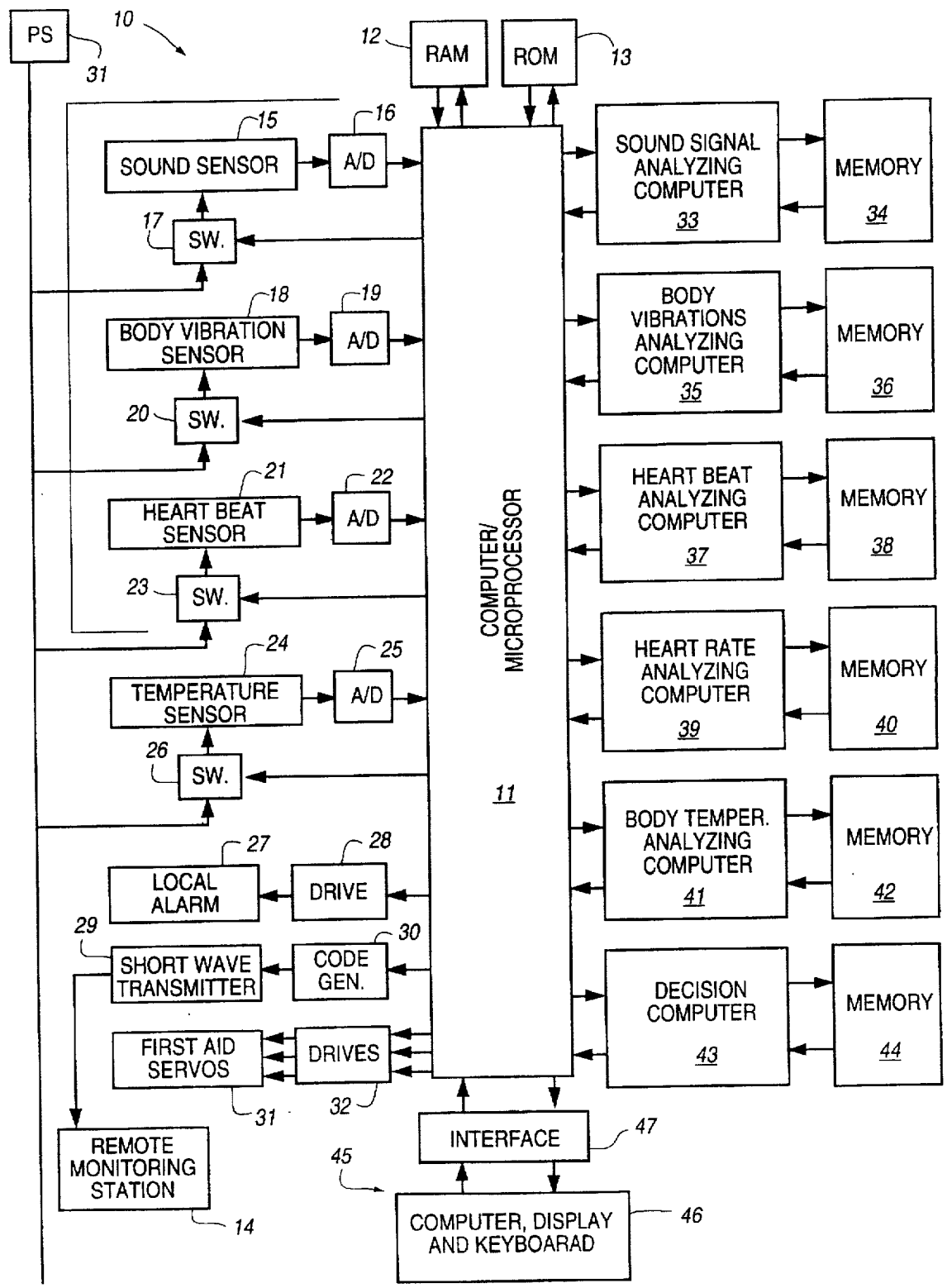

PATIENT MONITORING SYSTEM

This application is a continuation of application Ser. No. 08/221,045 filed on Mar. 31, 1994, now abandoned.

BACKGROUND AND SUMMARY OF THE INVENTION

This invention relates to systems and methods for monitoring physiological variables of patients. Most patient monitoring equipment in use today is relatively invasive, requiring the application of cannulas, mouthpieces, catheters, and other paraphernalia to the patient. Not only do such obtrusive devices tend to have an adverse psychological effect on the patient, but they may have physiologic effects as well. Such effects may affect the accuracy of any measurements taken.

In accordance with the invention, one or more sensors for measuring or detecting a physiological variable are disposed at or near the surface of the patient's body. Such physiological variables may include heart sounds, respiratory sounds, electrical activity of the heart (ie., an EKG), and body temperature. Digital signals corresponding to the physiological variable are generated from analog signals output by a transducer and fed to a computer which then passes them to a signal analyzing module (which may be a separate computer or a software module) for each type of physiological variable. The signal analyzing module then compares the digital signal with reference versions of the same signal and produces a coded signal in accordance with the comparison. The reference versions of the digital signals may, for example, correspond to the normal range of the physiological variable, prior measurements from the same patient, or to signs of specific pathology or condition. The coded signals generated by the signal analyzing module are next analyzed by a decision module (which may be a separate computer or a software module) which, from the information contained in such coded signals, generates an evaluation of the patient's present condition. If such evaluation indicates the need for medical treatment, the decision module activates a display or alarm to alert medical personnel or activates an actuation device for administering the treatment automatically under computer control.

It is therefore a primary object of the present invention to provide a system for monitoring one or more physiological variables of a patient and, from a computer analysis of the variables, generate an evaluation of the patient's condition.

It is a further object for the system to alert medical personnel when such evaluation indicates the need for further medical treatment or activate an actuator for administering medical treatment under computer control.

It is a further object for the system to monitor physiological variables by sensing body sounds of the patient.

Other objects, features, and advantages of the invention will become evident in light of the following detailed description considered in conjunction with the referenced drawings of a preferred exemplary embodiment according to the present invention.

BRIEF DESCRIPTION OF THE DRAWINGS

FIG. 1 is a block diagram of a system constructed in accordance with the invention.

DETAILED DESCRIPTION OF THE INVENTION

In FIG. 1 is shown a medical electronic system 10 for computer analyzing signals of physiological variables such as body sounds, vibrations, heart beat and temperature of a living being and detecting by such analysis the onset of a life threatening condition, such as a heart attack, apnea, stroke, grave degree of sickness, etc. System 10 employs one or more body sound or vibration sensors in sensing relation with the body of a living being, such as a person resting or sleeping on a mattress, pad or similar support which contains one or more sensors or transducers of one or more physiological variable associated with the body reclining or otherwise resting thereon. Prolonged monitoring of the physical condition of such living being is effected while the living being or person is asleep and/or awake and is in operable relation with respect to such transducer or transducers. When a deteriorating or life threatening condition is detected by one or more computers processing and analyzing generated by sensing body sounds and vibrations and, in certain instances, body temperature, select code signals are generated which may be employed to locally and/or remotely indicate to one or more persons that such condition exists and, in certain instances, the location of the person being monitored.

In my U.S. Pat. No. 4,299,233 entitled Patient Monitoring Device and Method discloses a cushioning device, in the form of a water filled mattress on which a baby, child or grown up person may recline and sleep. Disposed within the mattress and in contact with the water filling same, is a vibration pick-up or transducer for sensing body vibrations, such as heart beat and other sounds generated by a person reclining on the mattress, as illustrated in the drawings, wherein the resulting sensing signals are electronically analyzed and employed to activate an alarm when a serious body condition occurs. I also teach in such patent that body temperature may also be monitored by a temperature sensor supported within the mattress.

The instant invention employs a number of computing arrangements to not only detect the onset of a serious, life threatening physiological condition requiring medical attention but which may also operate to predict the onset of such a condition or a number of conditions some time before they occur to permit medical steps to be taken by a doctor or nurse and/or by a computer, to prevent the actual onset of the condition. Predictive computer circuitry and programmed software is provided to automatically analyze, on a continuous basis, signals output by one or more transducers sensing body variables and to predict and generate code signals indicative the nature and immanence of the serious condition or a plurality of select serious physiological conditions that will occur if select preventive steps are not taken by a medical attendant. In one form, a display indicates such information as the developing condition based on the computer analysis of the body signals. In another form, a speech signal generating computer operates to generate signals which are transduced to sounds of select words of speech by a remote and/or local speaker to inform a person present of the condition detected.

System 10 uses a power supply 31 and switches 17, 20, 23, and 25 to provide electrical power.

System 10 also employs a central controller in the form of a computer or microprocessor 11 having a RAM 12 and ROM 13 to which are connected various sensors and computers as well as devices controlled thereby. A body sound sensor 15, located in the mattress, pad or near the patient, senses body sounds and outputs analog signals which are digitized in an analog-to-digital (A/D) converter 16 wherein the resulting train(s) of digital signals are passed through the microprocessor 11 to a sound signal analyzing computer 33 which processes and compares such sound signals with recordings in its memory 34 to detect changes in body sounds, such as respiration sounds which are indicative of the onset and/or are predicative of the near future onset of a serious condition of the patient being monitored. Such computer analysis results in generation by computer 33 of code signals which are indicative of one or more body conditions, which signals are passed through computer 11 to a decision computer 43 connected also to computer 11.

A body vibration sensor 18 which may comprise sensor 15 or be separate therefrom, is supported by the mattress or a pad disposed beneath the patient, senses body vibrations caused by body movements, heartbeat and respiration and generates output analog electrical signals which are digitized in an A/D converted 19 and passed through microprocessor 11 to a body vibrations analyzing computer 35. Here again the trains of digital signals generated by detected body vibrations and/or movements are compared with code signals recorded in a memory 36 wherein computer 35 generates code signals which are indicative of a select physiological condition or the onset of a serious physical condition requiring medical attention.

A heart beat sensor 21, which may comprise or be part of the sound sensor 15 or may be separate therefrom and attached to the mattress or pad or to the patient, senses and generates output signals indicative of heart beat, which signals are digitized by an A/D converter 22 and passed through computer 11 to a heart beat analyzing computer 37 which queries its memory 38 and generates code signals on its output to microprocessor 11 which are passed to decision computer 43 or similar circuitry in a common computer operable to receive and analyze all physiological parameter sensing sensors. It is noted that sensors 15,18 and 21 may be separate sensors or may be combined in one sensing arrangement coupled to receive and transduce all body sounds and vibrations to analog electrical signals which may be computer analyzed as to their separate information contents. The output of A/D converter 23 is also passed to a heart rate analyzing computer 39 which generates output codes which are passed to computer 43 through microprocessor 11 for automatic analysis along with the digital codes generated by computers 33,35 and 37.

A body temperature sensor 24 is in temperature sensing relationship with the body of the patient and generates output analog signals indicative of body temperature which signals are digitized in an A/D converter 25 and passed through computer-microprocessor 11 to a body temperature analyzing computer 41 having a memory 42, which after analyzing same, generates code signals which it passes to computer 43 having a memory 42 through microprocessor 11.

As aforesaid, body sounds of the patient are detected via sound sensor 15 and/or vibration sensor 18 which produce digital signals in accordance with the sensed sounds or vibrations. Such digital signals are then analyzed by the sound signal analyzing computer 33 or body vibrations analyzing computer 35 which compare the digital signals with reference versions of the signals of the same signal and produce coded signals in accordance with the comparisons. The reference versions of the digital signals may, for example, correspond to the normal range of the particular physiological variable, to prior measurements from the same patient, or to a specific pathology or condition of the patient.

Examples of body sounds which may be detected by the present invention are respiratory sounds and heart sounds. In the case of the former, the signal analyzing computer produces coded signals representing the rate and rhythm of breathing by the patient derived from the respiratory sounds. Thus the system is able to detect abnormal breathing patterns such as apnea, tachypnea, hyperpnea (eg., Kussmaul breathing associated with metabolic acidosis), bradypnea, Cheyne-Stokes breathing, ataxic breathing, and obstructive breathing. Coded signals may also be generated from the respiratory sounds which indicate the presence of added lung sounds such as rales associated with pneumonia and pulmonary edema, wheezes associated with obstructive lung disease, and pleural rubs due to inflammation of the pleural membranes.

Coded signals derived from heart sounds are also produced by the signal analyzing computer which the represent the patient's heart rate and rhythm, magnitude and time relation of the first and second heart sounds due to the closure of the mitral and aortic valves, the presence of murmurs occuring in systole or diastole due to valvular abnormalities, and the presence of other abnormal heart sounds such as a pericardial friction rub due to inflammation of the pericardial sac.

Sensing devices and signal analyzing modules which are relatively more invasive than those illustrated in FIG. 1 may also be employed to measure physiological variables such as blood pressure, urinary output, blood gases, and the electical activity of the heart (ie., an EKG waveform). In the case of an EKG, coded signals are produced which represent not only the heart rate and rhythm (as in the case of heart sounds described above) but also abnormalities in the waveform which are indicative of cardiac dysfunction such as myocardial ischemia or abnormalities in the ionic composition of the patient's blood.

If the physical condition of the patient detected by the decision computer 43 as a result of comparing its computed information with information in its memory 44 is determined by such computer to indicate or predict the onset of a serious physical condition, such as a heart attach, apnea or other condition requiring immediate medical treatment, decision computer 43 generates control codes which are passed through computer 11 to (a) operate a local alarm 27 which may be located at bedside or in a nearby room, by driving or activating a drive 28 therefor; (b) activate a code generator 30 connected to a shortwave transmitter which is also energized thereby and generates and short wave transmits a select code to a remote monitor station 14 which, upon short wave receipt of such code applies same to an electronic display which displays the location of the patient to an attendant and/or to a speech signal generating computer which warns the attendant of the condition detected or predicted and the name or location of the patient.

Code signals output by the decision computer 43 may also be passed to one or more drives 32 for one or more solenoids or motors 31 operable to automatically operate in response thereto to operate one or more pumps, valves or other medical devices employed which apply first aid to the patient such as inject or pass a select amount of a drug or drugs into the patient too prevent or delay the onset of the serious change in physical condition requiring medical attention.

The decision computer 43 may also be operable to analyze the code signals it receives from the one or more auxiliary computers 33,35,37,39 and 41 it is connected to and generate code signals which define such variables and the identification of the serious condition detected and/or predicted thereby, the time predicted to the onset of same, a quantitative indication of the degree of the condition detected or predicted, etc. Such code signals may be passed through microprocessor 11 directly to the short wave transmitter to short wave same to the remote monitor station wherein the information defined by such codes is displayed on an electronic display or computer screen along with an indication of the patient's identity and location. Such latter code signals may also be employed to selectively control the operation of the first aid servos 31 or other corrective devices such as radiation and/or electrical energy applying devices operable to beneficially affect heart and/or lung operation, etc.

Moreover, microprocessor 11 may be linked by an interface 47 to other peripheral hardware. As shown in FIG. 1, microprocessor 11 may be linked through the interface to a display and/or keyboard 46.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A system for monitoring physiological variables of a patient and evaluating the patient's condition from the information contained therein comprising:

a sensor for transducing select physiological variables used to detect the onset of a select physical malady in said patient and producing analog signals in accordance therewith;

circuitry for processing said analog signals and converting same to digital signals;

a signal analysis computer in proximity with said patient, said signal analysis computer is used for analyzing said digital signals by comparing same with reference signals corresponding to the same physiological variable and said signal analysis computer is used to detect the onset of said select physical malady in said patient and producing first code signals in accordance with the comparison;

a decision computer for processing the first code signals produced by the signal analysis computer, evaluating same to determine if the onset of a physical malady will affect the patient's condition requiring medical treatment, and generating coded control signals indicative of the condition if such determination is made; and a short wave transmitter for receiving said coded control signals and short wave transmitting said coded signals to a monitor station wherein medical personnel will be alerted as to the onset of said select physical malady by an alarm.

2. A system in accordance with claim 1 wherein said sensor is operable to sense select physiological variables including respiratory sounds produced by the patient's breathing.

3. A system in accordance with claim 1 wherein said select physiological variables monitored by the system include an EKG waveform and further comprising an electronic display responsive to said code signals for displaying said waveform.

4. A system in accordance with claim 3 wherein said signal analysis computer produces code signals indicative of the patient's heart rate and rhythm and further comprising a display controlled by said code signals for displaying information defining said rate and rhythm.

5. A system in accordance with claim 1 wherein said select physiological variables monitored by the system include heart sounds and further comprising a display controlled by said code signals for displaying information defining said sounds.

6. A system in accordance with claim 5 wherein said signal analysis computer produces code signals indicative of the magnitude and time relation of sounds produced by the closing of heart valves and further comprising a display controlled by said code signals for displaying information defining said magnitude and time relation of sounds.

7. A system in accordance with claim 5 wherein said signal analysis computer produces code signals indicative of the presence of a heart murmur resulting from valvular abnormalities.

8. A system in accordance with claim 1 further comprising an actuator operated by said decision computer for administering a medical material to the patient.

9. A system in accordance with claim 8 wherein the medical material administered by said actuator is effected by the injection of a medication.

10. A system in accordance with claim 1 further comprising a local alarm activated by said decision computer when said decision computer indicates a need for immediate medical treatment.

11. A system in accordance with claim 1 further comprising a speech signal generator controlled in its operation by said decision computer for verbally communicating information relating to the patient's condition.

12. A system in accordance with claim 1 further comprising a monitor station remote from the patient and a radio receiver at said monitor station for receiving coded information relating to the patient's condition from said short wave transmitter and an electronic display responsive to the received information for indicating the patient's identity and location.

13. A system for monitoring the condition of a patient comprising:

a body sound sensor for transducing respiratory and heart sounds and producing audio signals in accordance therewith;

electronic circuitry for processing said audio signals and generating digital signals therefrom;

a signal analysis computer for analyzing said digital signals by electronically comparing said signals with reference signals corresponding to respiratory and heart sounds and producing code signals in accordance with the comparison;

a monitor station remote from said patient;

a decision computer for processing the code signals produced by the signal analysis computer, determining if the patient's condition requires medical treatment, and generating coded control signals indicative of the determination; and a short wave transmitter for transmitting said coded control signals to said monitor station wherein an alarm indicates that the patient's condition requires medical treatment.

14. A system in accordance with claim 13 wherein said sound signal analysis computer produces coded signals indicative of the presence of select lung sounds including rales, wheezes, and rubs.

15. A system in accordance with claim 13 further comprising:

a heart signal sensor for generating EKG waveform signals and producing digital EKG signals in accordance therewith; and a signal analyzing computer for analyzing said digital EKG signals by comparing said signals with reference versions of such signals and generating code signals in accordance with the comparison.

16. A system in accordance with claim 13 further comprising an actuator operated by code signals generated by said decision computer for administering a medical treatment to the patient and effecting a closed-loop control operation.

17. A system for monitoring physiological variables of a patient and evaluating the patient's condition from the information contained therein comprising:

- a sensor for transducing select physiological variables used to detect the onset of a select physical malady in the patient and producing analog signals in accordance therewith;
- circuitry for processing said analog signals and converting same to digital signals;
- a memory for receiving and storing said digital signals;
- a signal analysis computer in proximity with said patient, said signal analysis computer is used for analyzing said digital signals by comparing same with reference signals corresponding to the same physiological variable and said signal analysis computer is used to detect the onset of said select physical malady and producing first code signals in accordance with the comparison;
- a decision computer for processing the first code signals produced by the signal analysis computer, evaluating same to determine if the said physical malady will affect the patient's condition requiring medical treatment, generating coded control signals indicative of the condition if such determination is made, and generating additional coded control signals used to identify the location of said patient;
- a code generator responsive to said control signals output by said decision computer if such determination is made for generating code signals identifying the patient;
- a short wave transmitter for receiving and short wave transmitting said identifying code signals; and
- a short wave receiver for receiving said identifying code signals and means for intelligibly indicating the onset of the physical malady and the identity and location of the patient upon receipt of said identifying code signals.

18. A system in accordance with claim 17 wherein said identifying code signals indicate the location of the patient.

19. A system in accordance with claim 17 wherein said short wave receiver is at a remote monitor station.

20. A system in accordance with claim 18 further comprising means for intelligibly indicating the location of the patient upon receipt by said short wave receiver of code signals indicating the location of the patient.

* * * * *